(12) United States Patent
Nordby et al.

(10) Patent No.: US 8,147,469 B2
(45) Date of Patent: Apr. 3, 2012

(54) LAYERED ADHESIVE CONSTRUCTION WITH ADHESIVE LAYERS HAVING DIFFERENT HYDROCOLLOID COMPOSITION

(75) Inventors: Bolette Nordby, Hoersholm (DK); Danuta Ciok, Nivaa (DK)

(73) Assignee: Coloplast A/S, Humlebaek (DK)

( * ) Notice: Subject to any disclaimer, the term of this patent is extended or adjusted under 35 U.S.C. 154(b) by 902 days.

(21) Appl. No.: 12/087,990

(22) PCT Filed: Jan. 18, 2007

(86) PCT No.: PCT/DK2007/000024
§ 371 (c)(1),
(2), (4) Date: Jul. 18, 2008

(87) PCT Pub. No.: WO2007/082538
PCT Pub. Date: Jul. 26, 2007

(65) Prior Publication Data
US 2010/0286640 A1 Nov. 11, 2010

(30) Foreign Application Priority Data
Jan. 18, 2006 (DK) .................................. 2006 00078

(51) Int. Cl.
*A61F 5/44* (2006.01)
(52) U.S. Cl. ........ 604/336; 604/332; 604/337; 604/338; 604/343; 604/344; 604/346; 604/355
(58) Field of Classification Search .................. 604/336, 604/332, 337, 338, 343, 344, 346, 355
See application file for complete search history.

(56) References Cited

U.S. PATENT DOCUMENTS

| 3,339,546 | A | | 9/1967 | Chen | |
|---|---|---|---|---|---|
| 4,231,369 | A | * | 11/1980 | Sorensen et al. | 604/336 |
| 4,253,460 | A | * | 3/1981 | Chen et al. | 604/336 |
| 4,393,080 | A | * | 7/1983 | Pawelchak et al. | 428/355 R |
| 4,538,603 | A | | 9/1985 | Pawelchak et al. | |

(Continued)

FOREIGN PATENT DOCUMENTS

| EP | 0 092 999 A2 | 11/1983 |
|---|---|---|
| EP | 0 413 250 A1 | 2/1991 |

(Continued)

OTHER PUBLICATIONS

Table of Liquid Absorption Capacity (Annex 2 to Opposition filed Jun. 27, 2011—identified as "Other evidence").

*Primary Examiner* — Tatyana Zalukaeva
*Assistant Examiner* — Ginger T Chapman
(74) *Attorney, Agent, or Firm* — Jacobson Holman PLLC

(57) ABSTRACT

A layered adhesive construction comprising a backing layer and a first and second layer of hydrocolloid adhesive, where the first and second layer of hydrocolloid adhesive have different composition, and the second layer of hydrocolloid adhesive is at least partly interposed between the first layer of hydrocolloid adhesive and the backing layer, the first and second adhesive layers consisting of a continuous phase and a discontinuous phase where the discontinuous phase of the first adhesive layer comprises a hydrocolloids providing a higher moisture absorption capacity and higher initial rate of absorption to the adhesive layer than the hydrocolloids in the discontinuous phase of the second adhesive layer, and the discontinuous phase of second layer of adhesive comprises hydrocolloids providing a higher cohesion following moisture absorption to the adhesive compared to the hydrocolloid in the discontinuous phase of the first adhesive layer.

19 Claims, 1 Drawing Sheet

U.S. PATENT DOCUMENTS

| | | | |
|---|---|---|---|
| 4,551,490 A * | 11/1985 | Doyle et al. | 524/22 |
| 4,762,738 A * | 8/1988 | Keyes et al. | 428/34.3 |
| 4,775,374 A * | 10/1988 | Cilento et al. | 604/344 |
| 4,867,748 A | 9/1989 | Samuelsen | |
| 4,952,618 A * | 8/1990 | Olsen | 524/17 |
| 5,006,401 A * | 4/1991 | Frank | 442/151 |
| 5,051,259 A * | 9/1991 | Olsen et al. | 424/443 |
| 5,250,043 A * | 10/1993 | Castellana et al. | 604/336 |
| 5,492,943 A * | 2/1996 | Stempel | 523/111 |
| 5,534,561 A * | 7/1996 | Volke | 523/111 |
| 5,714,225 A * | 2/1998 | Hansen et al. | 428/114 |
| 6,326,421 B1 * | 12/2001 | Lipman | 524/22 |
| 6,451,883 B1 | 9/2002 | Chen et al. | |
| 6,471,575 B1 | 10/2002 | Hotani | |
| 6,685,683 B1 | 2/2004 | Clok et al. | |
| 6,726,791 B1 | 4/2004 | Øelund et al. | |
| 6,740,067 B2 * | 5/2004 | Leise et al. | 604/332 |
| 2003/0073965 A1 | 4/2003 | Leise, Jr. et al. | |

FOREIGN PATENT DOCUMENTS

| | | |
|---|---|---|
| EP | 0 686 381 A1 | 12/1995 |
| EP | 1 527 789 A1 | 5/2005 |
| JP | 58 190446 | 11/1983 |
| JP | 04 346921 | 12/1992 |
| JP | 2002 525219 | 8/2002 |
| WO | WO 94/15562 | 7/1994 |
| WO | WO 99/11302 | 3/1999 |
| WO | WO 00 18545 | 4/2000 |
| WO | WO 00/18554 | 4/2000 |
| WO | WO2007/076862 * | 7/2007 |

* cited by examiner

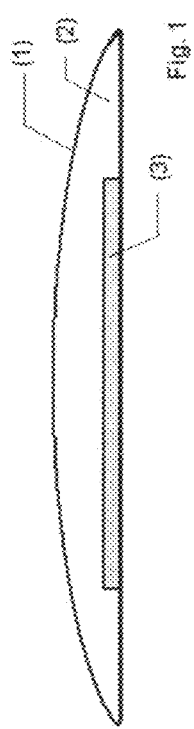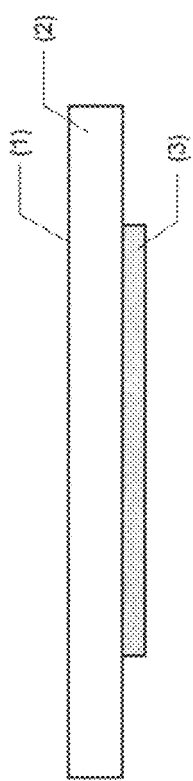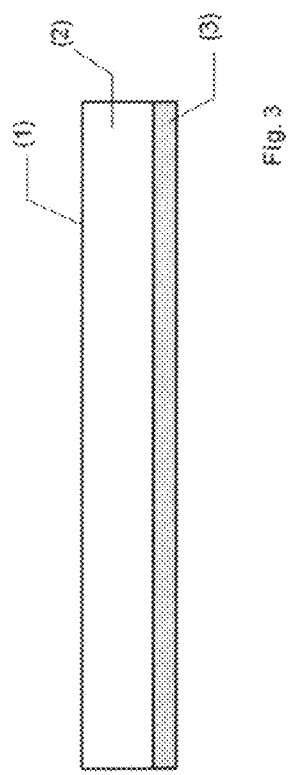

LAYERED ADHESIVE CONSTRUCTION WITH ADHESIVE LAYERS HAVING DIFFERENT HYDROCOLLOID COMPOSITION

This is a national stage of PCT/DK07/000024 filed Jan. 18, 2007 and published in English.

FIELD OF THE INVENTION

The present invention relates to an adhesive construction comprising at least two layers of hydrocolloid adhesives having a different composition. These adhesive constructions are useful for attaching medical devices, such as ostomy appliances, to the skin of patients.

In particular the invention relates to an adhesive construction with two adhesive layers, where the hydrocolloids in the first adhesive layer provides a higher initial moisture absorption capacity and rate of moisture absorption than the hydrocolloids in the second adhesive layer, which second layer on the other hand comprises hydrocolloids providing an improved cohesion following absorption of moisture to the adhesive compared to the hydrocolloids in the first adhesive layer. The first adhesive layer with hydrocolloids providing high moisture absorption capacity and high rate of absorption is used as skin contact surface, whereas the second adhesive layer with hydrocolloids providing moisture absorption as well as improved cohesion is at least partly placed away from the skin.

BACKGROUND OF THE INVENTION

Ostomy appliances of the so-called one-piece and two-piece types are commonly provided with adhesive faceplates for adhesively securing the appliances to the peristomal skin of the wearers, and moisture absorbing skin friendly hydrocolloid containing adhesives have been used as adhesives for these faceplates.

One early type of skin friendly adhesive is disclosed in U.S. Pat. No. 3,339,546 and consists of a blend of water-soluble and water swellable hydrocolloids, such as polyvinyl alcohol, pectin, gelatine and/or carboxymethyl cellulose and a water insoluble elastic binder, such as polyisobutylene. As the hydrocolloids absorb moisture, such a composition swells and begins to loose it integrity. In order to resist dissolution/disintegration, new hydrocolloid adhesive formulations were suggested, which included physically cross-linked elastomers, such as styrene-olefin-styrene block copolymers and tackifier, see U.S. Pat. No. 4,867,748.

U.S. Pat. No. 6,451,883 describes hydrocolloid adhesives comprising a polymer blend consisting of polybutene (in particular polyisobutylene) and a styrene block copolymer (in particular SIS), and a mixture of hydrocolloids, in particular a mixture of gelatine, pectin and carboxymethyl cellulose. According to this patent an adhesive may be prepared, which do not contain any tackifier or oil, by selecting an appropriate blend of polybutenes and styrene block copolymers.

The adhesive construction according to the invention comprises at least two layers of hydrocolloid adhesives, one adhesive layer with hydrocolloids providing a high moisture absorption capacity and fast initial absorption of moisture as the skin contact layer, and a second adhesive layer with hydrocolloids providing better cohesion than the first adhesive layer.

Adhesive constructions comprising layers of hydrocolloid adhesives are well known in the art:

EP 1 527 789 A1 describes a construction comprising a film layer and at least two layers of hydrocolloid adhesives with different composition.

The prime object of the adhesive construction described therein is to provide a multi-layered adhesive medical appliance that has the attributes of a skin friendly wet tack pressure sensitive adhesive for use adjacent the skin, and a flexible, comfortable, moisture tolerant adhesive that resists degradation after sterilization, and is capable of creating a seal around the stoma in a controlled fashion, for use away from the skin.

The adhesive for use adjacent to the skin is described as an adhesive comprising polyisobutylene and water-soluble or water swellable hydrocolloids.

The adhesive for use away from the skin is described as an adhesive comprising polyisobutylenes or blends of one or more polyisobutylenes and butyl rubber, one or more styrene radial or block type copolymers, mineral oil, one or more water soluble hydrocolloid gums and a tackifier.

It is described that a disadvantage of the known skin-friendly adhesives used adjacent to the skin is that they tend to be somewhat rigid when they become too thick. Thus, it is preferred that the adhesive layer adjacent to the skin is thinner than the more flexible, comfortable, moisture tolerant adhesive, which is used away from the skin.

The layered adhesive construction according to the invention differ from the construction described in EP 1 527 789 A1 in that the characteristic of the hydrocolloids are different in the two layers and in that the continuous phase (see below) is identical or essentially identical in the two layers.

EP 686 381 B2 describes similar adhesive constructions with two layers of hydrocolloid adhesives with different composition. According to this patent, the layer of adhesive securing the adhesive construction to the skin is composed of a skin friendly hydrocolloid containing adhesive that has a relatively low resistance to dissolution and/or disintegration when contacted by stomal fluids, whereas the other adhesive layer placed away from the skin is composed of a relatively soft, easy-deformable and extrudable, adhesive sealant material that is more resistant to dissolution or disintegration by stomal fluids than the material of the skin contact adhesive. From the drawings it is clear that the adhesive layer adjacent to the skin is thinner than the adhesive layer placed away from the skin.

Again the layered adhesive construction according to the invention differs from the construction described in EP 686 381 in that the characteristics of the hydrocolloids are different in the two layers and in that the continuous phase is identical or essentially identical in the two layers of adhesive.

EP 413 250 A1 describes an adhesive construction for use e.g. as part of an ostomy device, which comprises a backing layer and two layers of hydrocolloid adhesive. According to this document, both adhesive layers are in contact with the skin, the adhesive layer contacting the skin in the central part of the device being more than twice as thick as the adhesive layer contacting the skin in the peripheral portion of the construction.

It is indicated that the continuous phase of the two adhesive layers may be the same or may be different. Two different compositions, where the polymeric or continuous phase is different and the blend of hydrocolloids is identical, but present in different amounts, are mentioned for the adhesive layers.

U.S. Pat. No. 4,538,603 also describes an adhesive construction comprising two adhesive layers, which are of different composition, and where the adhesive layer intended for skin contact is thicker than the adhesive layer placed away from the skin. The adhesive layer placed away from the skin is relatively thin and bonded to a foam layer carrying a film on the surface facing away from the adhesive layer. The adhesive construction described herein is constructed be useful for covering exudating wounds or ulcers. It is described that the relatively thick skin contact layer, is composed of ingredients permitting the adhesive construction to remain in place on the skin for several days. The water dispersible hydrocolloids, the water swellable cohesive strengthening agents and the hydratable polymers distributed throughout the adhesive layer gradually becomes hydrated over time. Eventually the adhesive layer becomes so hydrated that the construction can be removed without stripping or macerating the skin around the wound site. The relatively thick adhesive layer to be placed on the skin comprises thermoplastic elastomer, such as low molecular weight polyisobutylene, and hydrocolloids, water swellable cohesive strengthening agents and hydratable polymers, whereas the relatively thin adhesive layer placed away from the skin and bonded to the foam layer may also comprise plastizisers and tackifiers.

Again, the two layers of hydrocolloid adhesives have different continuous phase.

WO 94/15562 describes adhesive constructions consisting of two adhesives, where one adhesive constitutes a layer in the form of an island embedded into the other adhesive layer. It is described how the additional material unit which makes up the island may be of a less cohesive material than the adhesive material making up the rest of the construction.

It is also described how the difference in cohesiveness in the two adhesives used is achieved by using a different continuous phases for the two adhesives, while the mixture of hydrocolloids remains the same in the two layers.

The layered adhesive construction according to the invention differ from the known layered adhesive constructions in that the discontinuous phase (or the hydrocolloids) is different in the two layers, in that the continuous phase of the adhesive is identical or essentially identical for the two layers of hydrocolloid adhesive and/or in that the skin contact adhesive layer is thinner than the adhesive layer interposed between the backing layer and the skin contact adhesive layer.

The adhesive construction according to the invention comprises at least two adhesive layers, one first adhesive layer with hydrocolloids providing a high initial moisture absorption capacity and fast absorption of moisture to the adhesive as the skin contact layer, and a second adhesive layer comprising hydrocolloids providing a good moisture absorption capacity and improved cohesion following absorption compared to the first adhesive layer. The second adhesive layer is at least partly placed behind the first adhesive layer and away from the skin, and is preferably thicker than the first adhesive layer. The thicker second layer of adhesive provides together with its absorption capacity, an effective transportation of moisture from the first adhesive layer and into the second adhesive layer, whereby disintegration and formation of pools of disintegrated adhesive between the skin and the first adhesive layer is diminished.

Due to the absorption capacity of the second adhesive layer, it will swell once it begins to absorb moisture from the first adhesive layer or possibly other sources. This is a particular advantage when the adhesive construction of the invention has a hole for receiving a stoma and is used as a faceplate for an ostomy appliance, because the second adhesive layer may swell and act to provide a seal in a situation where the first adhesive layer has become partly disintegrated in an area around the stoma.

By selecting the same continuous phase for the two adhesive layers, the layers become fully compatible with each other and migration of components from one layer into the other is avoided.

SUMMARY OF THE INVENTION

Thus, the present invention relates to a layered adhesive construction comprising a backing layer and a first and second layer of a hydrocolloid adhesive, where the first and second layer of hydrocolloid adhesive have different composition, and the second layer of hydrocolloid adhesive is at least partly interposed between the first layer of hydrocolloid adhesive and the backing layer, the first and second adhesive layers consisting of a continuous phase and a discontinuous phase, where
a) the discontinuous phase of the first adhesive layer comprises hydrocolloids providing a higher moisture absorption capacity and higher initial rate of moisture absorption to the adhesive than the hydrocolloids in the discontinuous phase of the second adhesive layer, and
b) the discontinuous phase of the second adhesive layer comprises hydrocolloids providing a higher cohesion following moisture absorption than the hydrocolloids in the discontinuous phase of the first adhesive layer.

BRIEF DESCRIPTION OF THE DRAWINGS

FIG. 1 shows a side view of an embodiment of the invention.

FIG. 2 shows a side view of a second embodiment of the invention.

FIG. 3 shows a side view of a third embodiment of the invention.

DETAILED DESCRIPTION OF THE INVENTION

As used herein "discontinuous phase" means the hydrocolloid(s) or mixture of hydrocolloids and any other particulate solids in the adhesive layers, such as filler (native starch), colours etc.

As used herein "continuous phase" means the total adhesive composition except the discontinuous phase as defined above.

As used herein "a higher cohesion following moisture absorption" in relation to two hydrocolloid adhesives, means a lower degree of disintegration/dissolution of the adhesive when the adhesives are exposed to water under the same conditions.

The difference in cohesion of adhesives may be evaluated by covering dimensionally identical samples of adhesives with saline (0.9%) at a temperature of 37° C. for a period of time (suitable 18 hours) and then evaluating the cohesiveness visually and by touching and manipulating the samples to evaluate whether and to what degree disintegration or dissolution has taken place.

The "absorption capacity" is the amount of water absorbed when the adhesive has been saturated with water. The absorption capacity may be measured by mounting dimensionally identical samples (e.g. a 25×25 mm sample which is 1 mm thick) on a glass plate and covering the samples with saline (0.9%) at 37° C.±2° C. and weighing the sample (after liquid on the surface of the sample has been wiped off) after 5 min, 10 min, 20 min 30 min, 60 min and 120 min, or until there is no further increase in weight and then calculating the absorption capacity as the weight of water absorbed per weight unit of adhesive, or per area unit of adhesive, when the adhesive is saturated with water.

As used herein "initial rate of absorption" is the rate of absorption at 5 minutes. The initial rate of absorption may be measured by mounting dimensionally identical samples (e.g. a 25 ×25 mm sample which is 1 mm thick) on a glass plate and covering the samples with saline (0.9%) at 37° C.±2° C. for 5 minutes and weighing the sample after liquid on the surface of the sample has been wiped off, and then calculating the increase in weight per weight unit adhesive or per area unit of adhesive and calculating the rate of absorption in the first 5 minutes by dividing with 5.

As used herein a "faceplate for an ostomy appliance" means a planar adhesive construction useful for attaching a bag to the peristomal skin of a patient and for protecting the skin surrounding the stoma.

The hydrocolloids in the adhesive layers may be on single type of hydrocolloid or a mixture of hydrocolloids.

Suitably, the hydrocolloids (or the mixture of hydrocolloids) in the first and second layer of the adhesives are different.

The continuous phases of the first and of the second adhesive layers are suitable identical or essentially identical.

As used herein "essentially identical" means that other components can be present in minor amounts in one continuous phase compared to the other continuous phase (less than 0.5% deviation pr component from one continuous phase to the other) and/or there is a minor deviation in the composition of the two continuous phases, such that each constituent of one phase is present ±0.5% in the other phase.

According to a preferred embodiment of the invention, the first layer of hydrocolloid adhesive comprises hydrocolloids, which are capable of absorbing a high amount of moisture at a high initial rate of absorption, i.e. a hydrocolloid such as carboxymethylcellulose (in particular sodium carboxymethyl cellulose) or another hydrocolloid providing similar absorption capacity and high initial rate of absorption to the adhesive. A disadvantage of such an adhesive composition is that the adhesive has a tendency to disintegrate following absorption of moisture, in particular if the moisture is not effectively transported through and away from the adhesive layer.

The second layer of the adhesive construction of the invention comprises a hydrocolloid providing a high cohesion to the adhesive following absorption of moisture, such as guar gum or other hydrocolloids providing similar good absorption and cohesion following absorption to the adhesive. Preferably, the second layer of adhesive is thicker than the first layer whereby the absorption capacity of the adhesive layer as such increases.

The combination of the two layers where the first adhesive layer, which is in contact with the moisture on the skin, has a high and fast initial moisture absorption with a layer of hydrocolloid adhesive which is capable of absorbing large amounts of moisture while preserving its integrity (high cohesion), provides an adhesive construct where moisture is effectively taken up by the first adhesive layer and transported thought the first layer of adhesive and into the second layer of adhesive. This means that the wet tack of the first adhesive layer is preserved and the disintegration thereof diminished.

The first adhesive layer need not be particularly thick and is preferably thinner than the second adhesive layer.

The hydrocolloids used in the layers of the adhesive construction of the invention may be selected from natural, synthetic and semi-synthetic hydrocolloids. Hydrocolloids useful in adhesives are well known in the art. Suitable water soluble and water swellable hydrocollids includes carboxymethyl cellulose (e.g. sodium carboxymetyl cellulose), pectin, gelatine, guar gum, locust bean gum, gum karaya, etc.

According to one embodiment of the invention, the discontinuous phase of the first adhesive layer comprises 40-50% w/w, preferably 45% w/w (based on the weight of the discontinuous phase) of sodium carboxymethylcellulose or a hydrocolloid providing similar absorption capacity and initial rate of absorption to the adhesive, and the discontinuous phase in the second adhesive layer comprises 35-45% w/w, preferably 40% w/w (based on the weight of the discontinuous phase), of guar gum or a hydrocolloid providing similar absorption capacity and cohesion following moisture absorption to the adhesive.

Preferably, the discontinuous phase of the first adhesive layer comprises between 40 and 50% w/w, preferably 45% w/w of carboxymethyl cellulose (suitably sodium carboxymethyl cellulose) and the discontinuous phase of the second adhesive layer comprises between 35 and 45% w/w, preferably 40% w/w of guar gum and 15-25% w/w, preferably 20% w/w carboxymethyl cellulose (e.g. sodium carboxymethyl cellulose).

The hydrocolloids in the first adhesive layer in any of the embodiments above, is suitably a mixture of pectin, gelatine and carboxymethylcellulose (suitably sodium carboxymethyl cellulose) and the hydrocolloids in the second adhesive layer is suitably a mixture of guar gum, gelatine and carboxymethylcellulose (e.g sodium carboxymethyl cellulose).

The hydrocolloids in the discontinuous phase of first adhesive layer, suitably comprises a mixture of:
40-50% w/w, preferably 45% w/w of carboxymethyl cellulose (e.g sodium carboxymethyl cellulose)
15-25% w/w, preferably 20% w/w pectin, and
30-40% w/w, preferably 33-35 5 w/w gelatine based on the weight of the discontinuous phase.

The hydrocolloids in the discontinuous phase of the second adhesive layer, suitably comprises a mixture of:
35-45% w/w, preferably 40% w/w of guar gum,
15-25% w/w, preferably 20 w/w carboxymethyl cellulose (e.g sodium carboxymethyl cellulose), and
35-45% w/w, preferably 40% w/w gelatine based on the weight of the discontinuous phase.

The, first adhesive layer suitably comprises 45-55% by weight of the discontinuous phase, preferably 50% of the discontinuous phase.

The second adhesive layer also suitably comprises 45-55% by weight of the discontinuous phase, preferably 50% of the discontinuous phase.

The composition of the polymer matrix of the first and second adhesive layer is preferably identical or essentially identical.

The continuous phase of the two adhesive layers may be any known polymer composition providing a pressure sensitive adhesive suitable for attachment to the skin.

Preferably, the continuous phase consist of a mixture of a styrene block copolymer with a liquid viscous polyolefin, such as polyisobutylene. The need for oil to soften the styrene blocks and the tackifier to improve the adhesive properties of the continuous phase, may be avoided by selecting the appropriate blend of styrene block copolymer in relation to the amount of liquid viscous polymer, see U.S. Pat. No. 6,451, 883.

According to another embodiment of the invention, the continuous phase mentioned above may contain up to 15% w/w of tackifier resin, oil etc.

According to a preferred embodiment of the invention, the continuous phase comprises 15-25% w/w, preferably about 20% w/w styrene block copolymer, such as Kraton D1107, Kraton D-1161 NU or similar styrene block copolymers and 75-85% w/w, preferably 80 w/w liquid viscous polyisobutylene, such as Oppanol B 12 SFN.

Such compositions are described in U.S. Pat. No. 6,541,883.

In one embodiment of the invention the second adhesive layer is extending beyond the peripheral edge of the first adhesive layer, and may contact the skin beyond the area where the first adhesive layer contacts the skin. According to this embodiment of the invention, the first adhesive layer may be thinner than the second adhesive layer and the first adhesive layer may be embedded in the second adhesive layer. This embodiment of the invention is illustrated in FIG. 1 showing the backing layer (1), the second adhesive layer (2) and the first adhesive layer (3).

As used herein "embedded" means that one layer is embedded in the other layer in such a way that only one of the surfaces of embedded layer is not covered by the other layer. These adhesive constructions may be prepared as described in WO 00/18554.

In another embodiment of the invention the second adhesive layer is attached on top of the first adhesive layer and the second adhesive layer is extending beyond the peripheral edge of the first adhesive layer, and may contact the skin beyond the area where the first adhesive layer contacts the skin. This is illustrated in FIG. 2 showing the backing layer (1), the second adhesive layer (2) and the first adhesive layer (3). Suitably, the first adhesive layer is thinner than the second adhesive layer.

The first and second adhesive layer may have the same area and shape and be aligned on top of each other. Again, the first adhesive layer is preferably thinner than the second adhesive layer see FIG. 3 showing the backing layer (1), the second adhesive layer (2) and the first adhesive layer (3). These adhesive constructions are prepared by preparing the layers separately and laminating the second adhesive layer between the backing layer and the first adhesive layer.

Suitably, the thickness of the first adhesive layer is suitably 0.1-0.4 mm, preferably 0.25-0.35 mm, or more preferred 0.3 mm and the thickness of the second adhesive layer interposed between the backing layer and the first adhesive layer is suitably between 0.5-1 mm, preferably 0.5-0.9 mm, more preferred 0.5-0.8 mm, or more preferred 0.5-0.7 mm.

The adhesive construction according to the invention may have bevelled peripheral edges where both adhesive layers are bevelled, or in case the second adhesive layer is extending beyond the peripheral edges of the first adhesive layer, only the second adhesive layer is bevelled. This is illustrated in FIG. 1. As indicated the second adhesive layer may become thinner than the first adhesive layer in the bevelled peripheral portion.

The surface of the adhesive layer (e.g. the second adhesive layer) attached to the backing layer is suitably covered completely by the backing layer.

The backing layer may be a thin polymeric film, film having multiple polymeric layers, a non-woven fabric, or an open celled or closed celled foam layer optionally having its outer surface covered by a film.

Suitable material for thin polymeric films include polyolefins, such as polyethylene, polypropylene, ethylene acrylic acids, ethylene vinyl acetates, polyvinylchlorides, polyether sulfones, polyether ketones, polyurethanes etc. The polymeric films are suitably impermeable to liquid water and may have a varying degree of water vapour permeability. Suitable non-woven fabrics include those made from polyester fibres, polypropylene fibres, nylon fibres, composite olefin fibres, or cellulose The thickness of the backing layer may vary depending on the material it is made of. The thickness of the backing layer is suitably 30-100 μm, preferably 40-70 μm.

The backing layer may also be a foam layer as described in U.S. Pat. No. 4,538,603. The backing layer may be of a weldable material so that other items or devices may be welded onto the backing layer.

Release liners the types well known in the art may be applied to the adhesive surface of the adhesive construction according to the invention. Such release liners are well known in the art.

The adhesive construction according to the invention may contain additional adhesive layers, additional film layers or other layers.

According to a further embodiment of the invention, the layered adhesive construction has a pattern of indentations in the form of groves in the surface provided with the backing layer.

These groves improve the flexibility of the adhesive construction and are formed in the adhesive layer(s) nearest to the backing layer (e.g the second adhesive layer), leaving the backing layer and the skin contact adhesive layer intact. The depth of the groves is preferably smaller than the thickness of the adhesive layer(s) nearest the backing layer, e.g. the second adhesive layer.

According to one embodiment, the indentations are extending radically from the center of the layered adhesive construct towards the periphery of the layered adhesive construct. Optionally the adhesive construct also has curvilinear indentations, which are crossing the radial indentations.

The use of indentations to improve the flexibility of an adhesive construct has been described in WO 04/087004.

EXPERIMENTALS

Materials

Oppanol B 12 SFN, a polyisobutylene from BASF, MW: 60.000-80.000
Kraton D-1161 NU, a SIS block copolymer from KRATON Polymers
Akucell AF 2881, sodium carboxymethyl cellulose from AKZO
Gelatine UF 220 from PB Gelatins
Guar Gum FG-200 from Nordisk Gelatine
Pectin Pomosin LM 12 CG-Z/200 from Copenhagen Pectin
Bayferrox, $Fe_2O_3$ obtainable from Bayer.

Example 1

Composition of second adhesive layer:

| Ingredient | Amount in gram |
| --- | --- |
| Oppanol B 12 SFN | 40 |
| Kraton D-1161 NU | 10 |
| Akucell AF 2881 | 10 |
| Gelatine UF 220 | 20 |
| Guar Gum FG-200 | 20 |

Example 2

Composition of first adhesive layer:

| Ingredient | Amount in gram |
|---|---|
| Oppanol B 12 SFN | 40 |
| Kraton D-1161 NU | 10 |
| Pectin Pomosin LM 12 CG-Z/200 | 10 |
| Akucell AF 2881 | 22.5 |
| Gelatine PB 220 | 17.47 |
| Bayferrox | 0.03 |

Example 3

The hydrocolloid adhesives may be prepared by heating the ingredients in a Z-mixer according to methods well known in the art and the layered adhesive construction may be prepared according to the method described in WO 00/18545.

Four clinical studies were performed using the layered adhesive construction.

Example 4

In study DK 151 OS (Approved by Freiburger ethic-kommision, Study Code: DK145OS, Feci Code: 05/1609) 64 German individuals with an ileostomy tested the layered adhesive construction with a drainable bag comparing it to a reference product, Moderma Flex "air space technology" single layer adhesive from Hollister inc. The study was an open, randomised, comparative, crossover multi-centre study. The study showed that participants experienced less erosion with the layered adhesive, 77% experienced a little or no erosion with the layered adhesive and 55% for the reference. Also immediate adhesion to the skin (tack) was deemed significantly better with the layered adhesive experienced by 83%, whereas it was 55% for the reference, as well as less pain when removing the layered adhesive compared to the reference.

Example 5

In the Feasibility study DK 153 OS (Approved by Comite Consulatatif de Protection des Personnes dans la Recherché Biomedicale de haute Normandie Aug. 12, 2005 sous le no 2005/031) 59 French individuals with an ileostomy tested the layered adhesive construction with a drainable bag comparing it to a reference product, Esteem with Invisiclose from Convatec. The study was an open, randomised, comparative cross-over study. The study showed that the immediate adhesion to the skin (tack) was found to be "good" or "very good" with the layered adhesive by 93% of participants compared to 66% for the Esteem adhesive. Adhesion during use was also experienced to be "good" or "very good" by 76% with the layered adhesive, which was significantly better than the 45% experienced for the Esteem adhesive. Immediate adhesion and adhesion during use are linked to initial rate of water absorption and water absorption after 120 minutes. The study also showed that participants experienced significantly less adhesive residues left on the skin when using the layered adhesive. Also a significantly better feeling of security was experienced with the layered adhesive construction.

Example 6

In the Feasibility study DK 109 OS (Approved by Regionale Videnskabsetiske Komité ØST J.nr.: 2005-2-07G) 68 Danish individuals with a colostomy tested the layered adhesive construction with a closed bag. The product was tested against the comparator, Nova 1, with a single layer adhesive from Dansac NS. The study was a randomized, comparative crossover-study. The study showed that the immediate adhesion to the skin (tack) and adhesion during use was significantly better when using the layered adhesive construction compared to the reference product (Immediate adhesion $p<0.0001$ and Adhesion during use $p<0.0175$). Immediate adhesion and adhesion during use are linked to initial rate of water absorption and water absorption after 120 minutes. Pain when removing the bag was also found to be significantly less compared to the reference product as well at the general feeling of security.

Example 7

In Feasibility study DK 145 OS (Approved by Freiburger ethic-commission, Study Code: DK145OS, Feci Code: 05/2099) 69 German individuals with a colostomy tested the layered adhesive construction with a closed bag. The product was tested against the comparator, Moderma Flex from Hollister. The study was a randomised comparative, crossover-study. The study showed that the immediate adhesion to the skin (tack) was significantly better when using the layered adhesive construction compared to the reference product ($p<0.0001$).

As mentioned earlier, the first adhesive layer with hydrocolloids providing high moisture absorption capacity and high rate of absorption is used as skin contact surface, whereas the second adhesive layer with hydrocolloids providing moisture absorption as well as improved cohesion is at least partly placed away from the skin. That cohesion is stronger for the layered adhesive after being covered with water with 0.9% NaCl for 18 hours is shown in Test report from the Danish Technological institute journalnr. 1220519-02 fgu/eta. This is shown for each of Convatec, Dansac A/S and Hollister adhesives.

The invention claimed is:

1. A layered adhesive construction comprising a backing layer and a first and second layer of hydrocolloid adhesive, where the first and second layer of hydrocolloid adhesive have different composition, and the second layer of hydrocolloid adhesive is at least partly interposed between the first layer of hydrocolloid adhesive and the backing layer, the first and second adhesive layers each having a continuous phase and a discontinuous phase, wherein
   a) the discontinuous phase of the first adhesive layer comprises a hydrocolloids providing a higher moisture absorption capacity and higher initial rate of absorption to the adhesive layer than the hydrocolloids in the discontinuous phase of the second adhesive layer,
   b) the discontinuous phase of second layer of adhesive comprises guar gum providing a higher cohesion following moisture absorption to the adhesive compared to the hydrocolloid in the discontinuous phase of the first adhesive layer, and
   c) the composition of the continuous phase of the first adhesive layer and of the continuous phase of the second adhesive layer are identical or essentially identical.

2. The layered adhesive construction according to claim 1, wherein the discontinuous phase of the first adhesive layer comprises 40-50% w/w of carboxymethylcellulose, and the discontinuous phase of the second adhesive layer comprises 35-45% w/w guar gum.

3. The layered construction according to claim 2 wherein the discontinuous phase of the first adhesive layer comprises between 40 and 50% w/w of carboxymethylcellulose.

4. The layered adhesive construction according to claim 2 wherein the discontinuous phase of the second adhesive layer comprises between 35 and 45% w/w of guar gum, and 15-25% w/w of carboxymethylcellulose.

5. The layered construction according to claim 1, wherein the discontinuous phase in the first adhesive layer comprises pectin, gelatine and sodium carboxymethyl-cellulose and the discontinuous phase in the second adhesive layer comprises guar gum, gelatine and sodium carboxymethyl cellulose.

6. The layered adhesive construction according to claim 5, wherein the first adhesive layer comprises a mixture of:
40-50% w/w of carboxymethyl cellulose,
15-25% w/w of pectin, and
30-40% w/w of gelatine,
based on the weight of the discontinuous phase,
and the second adhesive layer comprises a mixture of:
35-45% w/w of guar gum,
15-25% w/w, of carboxymethyl cellulose, and
35-45% w/w of gelatine,
based on the weight of the discontinuous phase.

7. The layered construction according to claim 1, wherein the first adhesive layer comprises 45-55% by weight of the discontinuous phase.

8. The layered construction according to claim 1, wherein the second adhesive layer comprises 45-55% by weight of the discontinuous phase.

9. The layered construction according to claim 1, wherein the first adhesive layer is thinner than the second adhesive layer at least in the area where the second adhesive layer is interposed between the backing layer and the first adhesive layer.

10. The layered construction according to claim 9, wherein the second adhesive layer is extending beyond the peripheral edge of the first adhesive layer.

11. The layered adhesive construction according to claim 10 wherein the first adhesive is thinner than the second adhesive layer and is embedded in the second adhesive layer.

12. The layered adhesive construction according to claim 10 wherein the second adhesive layer is placed on top of the first adhesive layer.

13. The layered construction according to claim 9, wherein the first and second adhesive layer have the same area and shape and are aligned on top of each other.

14. An ostomy appliance comprising an adhesive construction according to claim 1.

15. The layered construction according to claim 3, wherein the discontinuous phase of the first adhesive layer comprises 45% w/w of carboxymethyl cellulose.

16. The layered adhesive construction according to claim 4, wherein the discontinuous phase of the second adhesive layer comprises 40% w/w of guar gum, and 20% w/w carboxymethyl cellulose.

17. The layered adhesive construction according to claim 6, wherein the first adhesive layer comprises a mixture of:
45% w/w of carboxymethyl cellulose,
20% w/w of pectin, and
33-35% w/w of gelatine,
based on the weight of the discontinuous phase,
and the second adhesive layer comprises a mixture of:
40% w/w of guar gum,
20% w/w of carboxymethyl cellulose and
40% w/w of gelatine,
based on the weight of the discontinuous phase.

18. The layered construction according to claim 7, wherein the first adhesive layer comprises 50% by weight of the discontinuous phase.

19. The layered construction according to claim 1, wherein the second adhesive layer comprises 50% by weight of the discontinuous phase.

* * * * *